United States Patent
Björk et al.

[11] Patent Number: 6,077,851
[45] Date of Patent: Jun. 20, 2000

[54] QUINOLINE DERIVATIVES

[75] Inventors: Anders Björk, Bjärred; Stig Jönsson, Lund; Tomas Fex, Lund; Gunnar Hedlund, Lund, all of Sweden

[73] Assignee: Active Biotech AB, Lund, Sweden

[21] Appl. No.: 09/296,519

[22] Filed: Apr. 22, 1999

Related U.S. Application Data

[60] Provisional application No. 60/083,066, Apr. 27, 1998.

[30] Foreign Application Priority Data

Apr. 27, 1998 [SE] Sweden .................... 9801474

[51] Int. Cl.[7] ............ A61K 31/4704; A61P 29/00; A61P 37/02; C07D 215/22
[52] U.S. Cl. ............................... 514/312; 546/155
[58] Field of Search .............. 514/312; 546/155

[56] References Cited

U.S. PATENT DOCUMENTS

| | | | |
|---|---|---|---|
| 4,547,511 | 10/1985 | Eriksoo et al. | 514/312 |
| 4,738,971 | 4/1988 | Eriksoo et al. | 514/312 |
| 5,580,882 | 12/1996 | Abramsky et al. | 514/312 |
| 5,593,005 | 1/1997 | Slavin et al. | 514/311 |
| 5,726,183 | 3/1998 | Nilsson | 514/312 |
| 5,728,713 | 3/1998 | Nilsson | 514/312 |

FOREIGN PATENT DOCUMENTS

| | | |
|---|---|---|
| 0059698 | 9/1992 | European Pat. Off. |
| 9218483 | 10/1992 | WIPO |
| 9524195 | 9/1995 | WIPO |
| 9524196 | 9/1995 | WIPO |

*Primary Examiner*—Evelyn Mei Huang
*Attorney, Agent, or Firm*—Browdy and Neimark

[57] ABSTRACT

The invention relates to compounds of general formula (I)

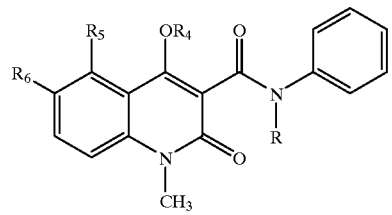

wherein R is selected from ethyl, n-propyl, iso-propyl, n-butyl, iso-butyl, sec.-butyl and allyl; $R_4$ is selected from hydrogen and pharmaceutically acceptable inorganic and organic cations; $R_5$ is selected from methyl, ethyl, n-propyl, iso-propyl, methoxy, ethoxy, chloro, bromo, $CF_3$, and $OCH_xF_y$; wherein x=0–2, y=1–3 with the proviso that x+y=3; $R_6$ is hydrogen; or $R_5$ and $R_6$ taken together are methylenedioxy; and any tautomer hereof. The invention also relates to pharmaceutical compositions containing a compound of the general formula (I) together with a pharmaceutically acceptable carrier. Included are also processes for the preparation of the compounds of formula (I), as well as methods of treating mammals suffering from diseases resulting from autoimmunity and pathological inflammation by administering a compound having the formula (I) to said mammal.

40 Claims, No Drawings

QUINOLINE DERIVATIVES

CROSS REFERENCE TO RELATED APPLICATION

This application claims the benefit of U.S. provisional application No. 60/083,066 filed Apr. 27, 1998.

FIELD OF THE INVENTION

The present invention relates to novel quinoline derivatives, to methods for their preparation, to compositions containing them, and to methods and use for clinical treatment of diseases resulting from autoimmunity such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease. More particularly, the present invention relates to novel quinoline derivatives suitable for the treatment of, for example, multiple sclerosis and its manifestations.

BACKGROUND OF THE INVENTION

Autoimmune diseases, e.g., multiple sclerosis (MS), insulin-dependent diabetes mellitus (IDDM), systemic lupus erythematosus (SLE), rheumatoid arthritis (RA), inflammatory bowel disease (IBD) and psoriasis represent assaults by the body's immune system which may be systemic in nature, or else directed at individual organs in the body. They appear to be diseases in which the immune system makes mistakes and, instead of mediating protective functions, becomes the aggressor (1).

MS is the most common acquired neurologic disease of young adults in Western Europe and North America. It accounts for more disability and financial loss, both in lost income and in medical care, than any other neurologic disease of this age group. There are approximately 250.000 cases of MS in the United States.

Although the cause of MS is unknown, advances in brain imaging, immunology, and molecular biology have increased researchers' understanding of this disease. Several therapies are currently being used to treat MS, but no single treatment has demonstrated dramatic treatment efficacy. Current treatment of MS falls into three categories: treatment of acute exacerbations, modulation of progressive disease, and therapy for specific symptoms. MS affects the central nervous system and involves a demyelination process, i.e. the myelin sheaths are lost whereas the axons are preserved. Myelin provides the isolating material that enables rapid nerve impulse conduction. Evidently, in demyelination, this property is lost. Although the pathogenic mechanisms responsible for MS are not understood, several lines of evidence indicate that demyelination has an immunopathologic basis. The pathologic lesions, the plaques, are characterised by infiltration of immunologically active cells such as macrophages and activated T cells (2).

In U.S. Pat. No. 4,547,511 and U.S. Pat. No. 4,738,971 and in EP 59,698 some derivatives of N-aryl-1,2-dihydro-4-substituted-1-alkyl-2-oxo-quinoline-3-carboxamide are claimed as enhancers of cell-mediated immunity. The compound

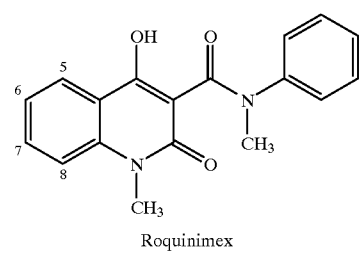

Roquinimex known as roquinimex (Merck Index 12$^{th}$ Ed., No. 8418; Linomide®, LS2616, N-methyl-N-phenyl-1,2-dihydro-4hydroxy-1-methyl-2-oxo-quinoline-3-carboxamide) belongs to this series of compounds. Roquinimex has been reported to have multiple immunomodulatory activities not accompanied with general immunosuppression (3–12).

Furthermore, in U.S. Pat. No. 5,580,882 quinoline-3-carboxamide derivatives are claimed to be useful in the treatment of conditions associated with MS. The particular preferred compound is roquinimex. In U.S. Pat. No. 5,594,005 quinoline-3-carboxamide derivatives are claimed to be useful in the treatment of type I diabetes. The particular preferred compound is roquinimex. In WO 95/24195 quinoline-3-carboxamide derivatives are claimed to be useful in the treatment of IBD. Particularly preferred compounds are roquinimex or a salt thereof. In WO95/24196 quinoline-3-carboxamide derivatives are claimed to be useful in the treatment of psoriasis. Particularly preferred compounds are roquinimex or a salt thereof.

In clinical trials comparing roquinimex to placebo, roquinimex was reported to hold promise in the treatment of conditions associated with MS (13, 14). There are, however, some serious drawbacks connected to roquinimex. For example, it has been found to be teratogenic in the rat, and to induce dose-limiting side effects in man, e.g., a flu-like syndrome, which prevents from using the full clinical potential of the compound.

Further, in WO 92/18483 quinoline derivatives substituted in the 6-position with a $R_A S(O)_n$-group ($R_A$=lower alkyl or aryl; n=0–2) are claimed, which possess an immunomodulating, anti-inflammatory and anti-cancer effect.

The substitution, i.e., type and pattern, of the above, specifically mentioned, compounds places them outside the scope of the present invention.

DESCRIPTION OF THE INVENTION

A primary objective of the present invention is to provide structurally novel quinoline compounds which by virtue of their pharmacological profile, with high potency in experimental models and low level of side-effects, are considered to be of value in the treatment of disease resulting from autoimmunity and pathologic inflammation. Examples of such diseases are multiple sclerosis, insulin-dependent diabetes mellitus, systemic lupus erythematosus, rheumatoid arthritis, inflammatory bowel disease and psoriasis and other diseases where inflammation plays a major role, such as asthma, atherosclerosis, stroke and Alzheimer's disease. More particularly, the present invention relates to novel quinoline derivatives suitable for the treatment of, for example, multiple sclerosis and its manifestations.

It has now surprisingly been found that the novel compounds of general formula (I)

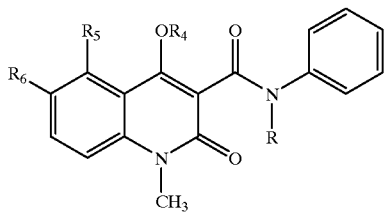

(I)

wherein
- R is selected from ethyl, n-propyl, iso-propyl, n-butyl, iso-butyl, sec.-butyl and allyl;
- $R_4$ is selected from hydrogen and pharmaceutically acceptable inorganic cations, such as sodium, potassium and calcium, and organic cations such as monoethanolamine, diethanolamine, dimethylaminoethanol, morpholine and the like;
- $R_5$ is selected from methyl, ethyl, n-propyl, iso-propyl, methoxy, ethoxy, chloro, bromo, $CF_3$, and $OCH_xF_y$;

wherein
x=0–2,
y=1–3 with the proviso that
x+y=3;
- $R_6$ is hydrogen; or
- $R_5$ and $R_6$ taken together are methylenedioxy;

are unexpectedly effective and specific in the treatment of individuals suffering from autoimmune and inflammatory diseases.

The compounds of general formula (I) may exist in different tautomeric forms and all such forms are included herein.

In a preferred embodiment of the invention $R_4$ is hydrogen or sodium, and $R_5$ is ethyl, methoxy, chloro or bromo, and $R_5$ and $R_6$ taken together are methylenedioxy, and R is ethyl or n-propyl, especially ethyl.

Several autoimmune diseases in man have experimental models that are spontaneously occurring in certain strains of laboratory animals or can be induced in laboratory animals by immunisation with specific antigen(s) from the target organ.

Experimental autoimmune encephalomyelitis (EAE) as a model for autoimmune inflammatory diseases of the central nervous system (CNS) has been the most widely used model for the human disease multiple sclerosis.

Autoimmunity to type II collagen can experimentally be induced in certain strains of mice or rats and may lead to the development of polyarthritis. The collagen-induced arthritis has several features in common with the human disorder rheumatoid arthritis.

The hallmark of asthma in humans is an increased reactivity of the airways to a range of chemical and physical stimuli. It is now widely accepted that products released from inflammatory cells, e.g., activated eosinophils, compromise epithelial integrity and promote bronchial hyperresponsiveness. The murine model of ovalbumin (OA)-induced lung inflammation is dominated by the temporally regulated influx of lymphocytes and eosinophils into the bronchial lumen.

Roquinimex has been found to induce the Beagle Pain Syndrome (BPS) (15, 16) in different breeds of beagle dogs. The disease is reflected by clinical and laboratory manifestations justifying BPS as a model for the flu-like syndrome induced by roquinimex in man.

The compounds of general formula (I) were assayed for inhibition of EAE in mice. Roquinimex was used as treatment control and showed a 70% inhibition at 5 mg/kg. Surprising and unexpected results were obtained when introducing proper substitution in the 5-position, e.g., 5-chloro, of the quinoline ring. In comparison with roquinimex, the potency was increased a 100-fold. Substitution in the 6-, 7-, and 8-position resulted in less active compounds. In general, the EAE activity as seen by the EAE inhibition was in the following descending order according to the position of the substitution: 5>6>>7=8. The effect of the 5-substitution could largely be understood on physiochemical grounds. Moreover, replacement of the methyl group on the carboxamide nitrogen with an ethyl group or further elongation of the alkyl group to a propyl or butyl group extinguished the teratogenic effect of roquinimex in the rat and significantly reduced the BPS. On the other hand, changing the R-group from alkyl to hydrogen decreased the water-solubility at physiological pH more than a $10^5$-fold. Replacement of the alkyl group also affected the pharmacokinetic properties. For example, in comparison with roquinimex the clearance (Cl) of compound A in dogs was an 800-fold higher.

Compound A

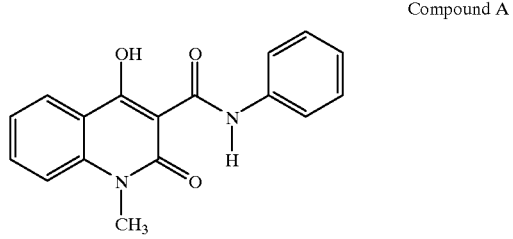

The solubility and pharmacokinetic issues significantly reduce the useful order of activity of this class (R=H) of compounds. Hence, the compounds of formula (I) have surprisingly been found to be both chemically and pharmacologically different from those drugs hitherto suggested for the treatment of MS and its manifestations.

The compounds of general formula (I) are prepared by the following methods:

Method A

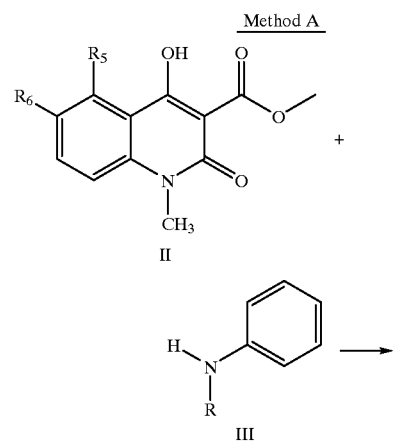

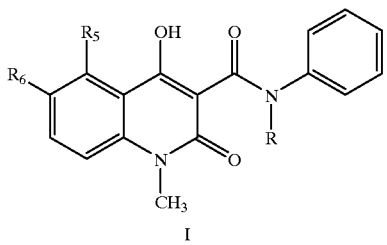

The compounds of formula (I) may be prepared by known methods, for example, by reaction of an ester derivative of the quinoline carboxylic acid (II) with an aniline (III) in a suitable solvent such as toluene, xylene and the like. Suitable esters are methyl and ethyl esters.

Method B

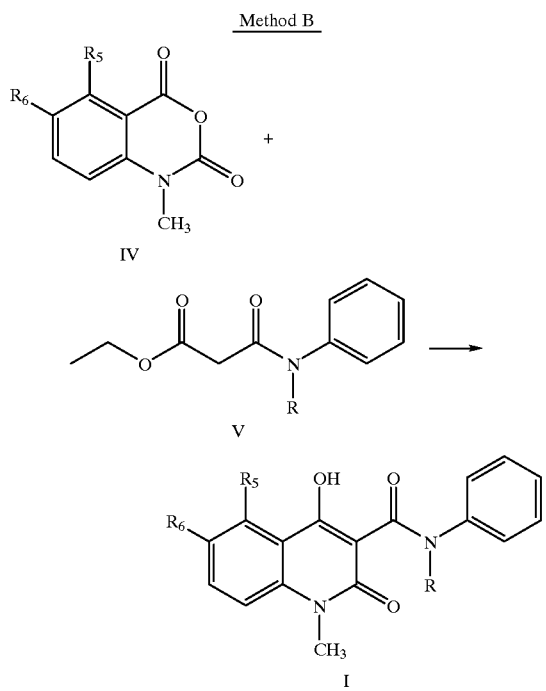

The compounds of formula (I) may also be prepared by reaction of an isatoic anhydride (IV) with an N-alkyl-N-phenylcarbamoyl acetic acid alkyl ester (V) using a strong base, e.g., sodium hydride in a suitable solvent such as N,N-dimethylacetamide. Suitable esters are methyl and ethyl esters.

Method C

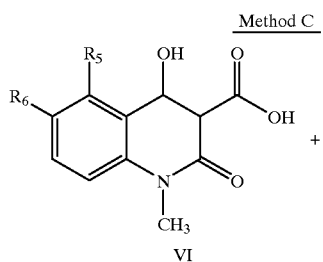

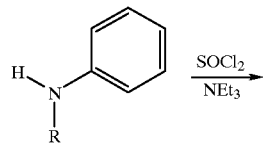

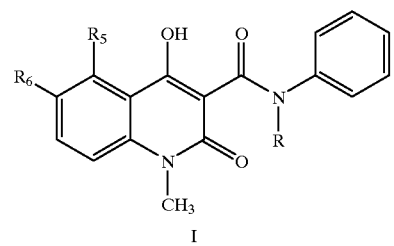

The compounds of formula (I) may also be prepared by reaction of a quinoline carboxylic acid of formula (VI) with an aniline of formula (III). Various coupling reagents known in the art may be used, e.g., carbodiimides known from U.S. Pat. No. 4,547,511. One suitable coupling method utilises thionyl chloride in the presence of triethylamine and a suitable solvent such as dichloromethane. This method may be used in instances when direct coupling between ester and aniline does not work. The quinoline carboxylic acids of formula (VI) may be obtained from the corresponding esters of formula (II) by acidic hydrolysis as described below.

The quinoline carboxylic esters (II) above may be prepared by the methods shown in examples 5–8 below. The quinoline carboxylic acids (VI) may be prepared by the method shown in example 9 below.

All embodiments of the invention as disclosed in the claims are herewith included in the specification.

The following examples are intended to illustrate the invention without restricting the scope thereof.

EXAMPLE 1

N-Ethyl-N-phenyl-1,2-dihydro-4-hydroxy-5-methoxy-1-methyl-2-oxo-quinoline-3-carboxamide (Method A)

N-Ethylaniline (3.0 g, 25 mmol) was dissolved in 80 ml of toluene and about 30 ml of the solvent was distilled off in order to obtain a dry solution. To this boiling solution was added 1,2-dihydro-4hydroxy-5-methoxy-1-methyl-2-oxo-quinoline-3-carboxylic acid ethyl ester (2.7 g, 10 mmol). The ethanol formed during the reaction was distilled off together with some toluene for about 4 hours. The reaction mixture was cooled to room temperature. The precipitate was collected, washed with cold toluene and hexane and dried to give the title compound (2.8 g), yield 80%.

$^1$H NMR (CDCl$_3$) δ 1.26 (3H, t), 3.50 (3H, s), 3.97 (2H, q), 4.03 (3H,s), 6.67 (1H, d), (6.87 (1H, d), 7.12–7.25 (3H, m), 7.36–7.44 (3H, m).

13C NMR (CDCl$_3$) δ 13.0 (CH$_3$), 29.6 (CH$_3$), 43.8 (CH$_2$), 56.8 (CH$_3$), 103.2 (CH), 104.2 (C), 108.3 (CH), 110.5 (C), 127.3 (2CH), 127.4 (CH), 128.5 (2CH), 131.2 (CH), 141.1 (C), 141.9 (C), 156.9 (C), 157.1 (C), 160.2 (C), 164.4 (C). ESI MS/MS [M+H]$^+$ 353, fragments 232 and 122.

In essentially the same manner the following compounds were obtained from the corresponding starting materials:

N-ethyl-N-phenyl-1,2-dihydro-1,5-dimethyl-4-hydroxy-2-oxo-quinoline-3-carboxamide.

$^1$H NMR (CDCl$_3$) δ 1.21 (3H, t), 2.83 (3H, s). 3.23 (3H, s), 3.98 (2H, q), 6.97 (1H, d), 7.02 (1H, d), 7.10–7.25 (5H, m), 7.39 (1H, t), 13.08 (1H, s).

13C NMR (CDCl$_3$) δ12.9 (CH$_3$), 24.4 (CH$_3$), 29.5 (CH$_3$), 45.9 (CH$_2$), 102.8 (C), 112.2 (CH), 114.3 (C), 125.5 (CH), 126.4 (2CH), 126.4 (CH), 128.4 (2CH), 131.7 (CH), 139.6 (C), 142.0 (C), 142.4 (C), 158.1 (C), 169.7 (C), 170.1 (C). ESI MS/MS [M+H]$^+$ 337, fragments 216 and 122.

N-ethyl-N-phenyl-1,2-dihydro-4-bydroxy-5-chloro-1-methyl-2-oxo-quinoline-3-carboxamide.

1H NMR (CDCl$_3$) δ 1.20 (3H, t), 3.28 (3H, s), 3.97 (2H, q), 7.08–7.25 (7H, m), 7.39 (1H, t), 12.6 (1H, s).

13C NMR (CDCl$_3$) δ 12.9 (CH$_3$), 29.8 (CH$_3$), 45.7 (CH$_2$), 105,0 (C), 112.7 (C), 113.3 (CH), 125.4 (CH), 126.7 (2CH), 126.8 (CH), 128.5 (2CH), 131.6 (CH), 132.7 (C), 142.0 (C), 142.6 (C), 157.9 (C), 165.6 (C), 168.7 (C). ESI MS/MS [M+H]$^+$ 357, fragments 236 and 122.

N-ethyl-N-phenyl-1,2-dihydro-4-hydroxy-5-fluoro-1-methyl-2-oxo-quinoline-3-carboxamide.

1H NMR (CDCl$_3$ +TFA) δ 1.28 (3H, t), 3.66 (3H, s), 3.93–4.05 (2H, m), 711 (1H, q), 7.26–7.37 (6H, m), 7.68 (1H, q), 11.42 (1H, s).

13C NMR (CDCl$_3$+TFA) δ 12.6 (CH$_3$), 31.4 (CH$_3$), 46.4 (CH$_2$), 104.4+104.5 (C), 108.7 (C), 110.4+110.5 (CH), 112.7+112.8 (CH), 126.8 (2CH), 129.7 (CH), 129.8 (2CH), 134.1+134.2 (CH), 139.9 (C), 141.0 (C), 158.0 (C), 159.3+161.3 (C), 161.4 (C), 166.8 (C); (Some peaks are doublets due to F-coupling). ESI MS/MS [M+H]$^+$ 341, fragments 220 and 122.

N-ethyl-N-phenyl-1,2-dihydro-4-hydroxy-5-trifluoromethyl-1-methyl-2-oxo-quinoline-3-carboxamide.

1H NMR (CDCl$_3$+TFA) δ 1.21 (3H, t), 3.30 (3H, s), 3.99 (2H, q), 7.10–7.25 (5H, m), 7.42 (1H, d), 7.60 (1H, t), 7.67 (1H, d), 13.05 (1H, s).

13C NMR (CDCl$_3$+TFA) δ 12.5 (CH$_3$), 31.1 (CH$_3$), 46.2 (CH$_2$), 106.4 (C), 113.0 (C), 119.5 (CH), 120+122.2+124.4 (CF$_3$), 123.4 (CH), 126.6 (2CH), 128.1 (CH), 128.1+128.3 (C), 129.1 (2CH), 132.1 (CH), 140.5 (C), 141.4 (C), 159.3 (C), 163.7 (C), 167.8 (C). ESI MS/MS [M+H]$^+$ 391, fragments 270 and 122.

N-ethyl-N-phenyl-1,2-dihydro-4-hydroxy-5-trifluoromethoxy-1-methyl-2-oxo-quinoline-3-carboxamide.

N-allyl-N-phenyl-1,2-dihydro-4-hydroxy-5-chloro-1-methyl-2-oxo-quinoline-3-carboxamide.

1H NMR (CDCl3) δ 3.33 (3H, s), 4.57 (2H, m), 5.22 (1H, d), 5.38 (1H, d), 6.0 (1H, m), 7.13–730 (7H, m), 7.44 (1H, t), 12.45 (1H, s).

N-allyl-N-phenyl-1,2-dihydro-4-hydroxy-5-methoxy-1-methyl-2-oxo-quinoline-3-carboxamide.

1H NMR (CDCl$_3$) δ 3.52 (3H, s), 4.04 (3H, s), 4.52 (2H, m), 5.20 (1H, d), 5.37 (1H, d), 6.02 (1H, m), 6.67 (1H, d), 6.88 (1H, d), 7.10–7.23 (3H, m), 7.38–7.45 (3H, m), 9.82 (1H, s).

N-phenyl-N-n-propyl-1,2-dihydro-4-hydroxy-5-methoxy-1-methyl-2-oxo-quinoline-3-carboxamide.

1H NMR (CDCl$_3$) δ 1.0 (3H, t), 1.65 (2H, m), 3.48 (3H, s), 3.9 (2H,t), 4.01 (3H, s), 6.65 (1H, d), 6.83 (1H, d), 7.1–7.25 (3H, m), 7.3–7.45 (3H, m), 9.8 (1H, s).

EXAMPLE 2

N-Ethyl-N-phenyl-1,2-dihydro-4-hydroxy-5-chloro-1-methyl-2-oxo-quinoline-3-carboxamide (Method B)

5-Chloro isatoic anhydride (5 g, 25 mmol) was dissolved in 50 ml of N,N-dimethylacetamide and cooled to 0° C. Sodium hydride (75%) (0.94 g, 1.1 eq.) followed by methyl iodide (1.89 ml, 1.2 eq.) was added at a rate to keep the temperature below 5° C. The reaction mixture was stirred at 20° C. for 5 hours whereupon the remaining methyl iodide was removed under vacuum. Sodium hydride (0.94 g, 1.1 eq.) was added together with N-ethyl-N-phenylcarbamoyl acetic acid ethyl ester (6.3 g, 1.1 eq.). The mixture was heated at 85° C. for 5 hours. After cooling to room temperature 50 ml of methanol and 50 ml of 1M hydrochloric acid and subsequently 250 ml of water were added. An emulsion was formed which crystallised on standing in a refrigerator for 72 hours. The crystalline mass was collected by filtration, washed with water, water/methanol (1:1) and heptane and dried to afford the title compound (6.12 g). The title compound was recrystallised from methanol in >95% purity.

N-Ethyl-phenyl-1,2-dihydro-4-hydroxy-5-chloro-1-methyl-2-oxo-quinoline-3-carboxamide sodium salt A solution of 5 M sodium hydroxide was prepared by dilution of a 50 weight-% sodium hydroxide solution (10.0 g) with sterile water to the total volume of 25 ml. N-Ethyl-N-phenyl-1,2-dihydro-4-hydroxy-5-chloro-1-methyl-2-oxo-quinoline-3-carboxamide (10.0 g) was suspended in ethanol (150 ml) and the previously prepared 5 M sodium hydroxide solution was added to pH 8–12 (5.6 ml). The reaction mixture was stirred for another 30 minutes at ambient temperature. The resulting precipitation was filtered off and rapidly washed twice with ethanol (2×150 ml). The precipitate was then dried in vacuum over P$_2$O$_5$ to give the title compound (9.5 g), yield 90%.

1H NMR (D$_2$O). Two isomers in ratio 1:4. δ 0.90 (3H, t, minor form), 1.10 (3H, t, major form), 3.21 (3H, s, major form), 3.50 (3H, s, minor form), 3.50–3.70 (2H, m, minor form), 3.70–3.85 (2H, m, major form), 6.92–7.51 (8H, m, both forms).

EXAMPLE 3

N-Ethyl-N-phenyl-1,2-dihydro-4-hydroxy-5-bromo-1-methyl-2-oxo-quinoline-3-carboxamide (Method C)

To an ice-cold solution of 1,2-dihydro-4-hydroxy-5-bromo-1-methyl-2-oxo-quinoline-3-carboxylic acid (9.6 g, 0.032 mol), triethylamine (15.5 ml, 0.11 mol) and N-ethylaniline (4.2 g, 0.035 mol) in 150 ml of dichloromethane was added dropwise during 0.5 hours a solution of thionyl chloride (3.0 ml, 0.042 mol) in 10 ml of dichloromethane. The stirring was continued at 4° C. for 24 hours. The solvents were evaporated. The residue was dissolved in ethyl acetate, filtered through celite and extracted with 2 M sodium hydroxide. The aqueous phase was washed with ethyl acetate and then acidified with hydrochloric acid to pH 5. On standing a crystalline precipitate was formed which was filtered off, washed with water and dried to give the title compound (8.5 g), yield 69%.

1H NMR (CDCl$_3$) δ 1.15–1.22 (3H, broad signal), 3.25 (3H, s), 3.95 (2H, s broad), 7.08–731 (7H, m), 7.43–7.50 (1H, m).

In essentially the same manner the following compounds were obtained from the corresponding starting materials:

N-ethyl-N-phenyl-1,2-dihydro-4-hydroxy-5,6-methylenedioxy-1-methyl-2-oxo-quinoline-3-carboxamide.

1H NMR (CDCl$_3$+TFA) δ 1.27 (3H, t), 3.57 (3H, s), 3.98 (2H, q), 6.23 (2H, s), 6.86 (1H, d), 7.19 (1H, d), 7.25–7.35 (5H, m), 10.3 (1H, s broad).

13C NMR (CDCl$_3$+TFA) δ 12.4 (CH$_3$), 30.9 (CH$_3$), 46.0 (CH$_2$), 101.6 (C), 103.7 (CH$_2$), 107.4 (C), 108.4 (CH), 113.7 (CH), 126.7 (2CH), 128.8 (CH), 129.3 (2CH), 134.1 (C), 140.1 (C), 143.1+143.2 (2C), 157.3 (C), 160.9 (C), 166.3 (C). ESI MS/MS [M+H]$^+$ 367, fragments 246 and 122.

N-ethyl-N-phenyl-1,2-dihydro-4-hydroxy-5-ethyl-1-methyl-2-oxo-quinoline-3-carboxamide.

1H NMR (CDCl$_3$) δ 1.26 (3H, t), 1.31 (3H, t), 3.20–3.34 (5H, m), 4.0 (2H, q), 7.02–7.07 (2H, m), 7.13–7.28 (5H, m), 7.44 (1H, t) 13.2 (1H, s broad).

13C NMR (CDCl$_3$) δ 13.2 (CH$_3$), 16.8 (CH$_3$), 29.8+30.2 (CH$_3$+CH$_2$), 46.1 (CH$_2$), 103.3 (C), 112.5 (CH), 113.9 (C), 124.6 (CH), 126.7+126.7 (3CH), 128.6 (2CH), 132.1 (CH), 142.3 (C), 142.6 (C), 146.2 (C), 158.3 (C), 169.3 (C), 170.4 (C). ESI MS/MS [M+H]$^+$ 351, fragments 230 and 122.

N-phenyl-N-iso-propyl-1,2-dihydro-4-hydroxy-5-chloro-1-methyl-2-oxo-quinoline-3-carboxamide.

1H NMR (CDCl$_3$) δ 1.24 (6H, d), 3.38 (3H, s broad), 5.09 (1H, broad signal), 7.08 (1H, d), 7.15 (1H, d), 7.15–7.34 (5H, m), 7.34 (1H, t), 11.1 (1H, s broad).

13C NMR (CDCl$_3$) δ 21.0 (2CH$_3$), 29.9 (CH$_3$), 48.2 (CH), 109.4 (C), 112.4 (C), 113.5 (CH), 125.1 (CH), 127.9 (2CH), 127.9 (CH), 129.6 (2CH), 131.1 (CH), 131.6 (C), 137.9 (C broad), 142.1 (C), 158.6 (C), 160.6 (C), 167.5 (C).

N-phenyl-N-(n-propyl)-1,2-dihydro-4-hydroxy-5-chloro-1-methyl-2-oxo-quinoline-3-carboxamide.

1H NMR (CDCl$_3$) δ 0.95 (3H, t), 1.58–1.69 (2H, m), 3.29 (3H, s broad), 3.88 (2H, broad), 7.08–7.26 (7H, m), 7.41 (1H, t), 12.5 (1H, s broad).

EXAMPLE 4

N-Ethyl-phenyl-1,2-dihydro-4-hydroxy-5-chloro-1-methyl-2-oxo-quinoline-3-carboxamide sodium salt A solution of 5 M sodium hydroxide was prepared by dilution of a 50 weight-% sodium hydroxide solution (10.0 g) with sterile water to the total volume of 25 ml. N-Ethyl-N-phenyl-1,2-dihydro-4-hydroxy-5-chloro-1-methyl-2-oxo-quinoline-3-carboxamide (10.0 g) was suspended in ethanol (150 ml) and the previously prepared 5 M sodium hydroxide solution was added to pH 8–12 (5.6 ml). The reaction mixture was stirred for another 30 minutes at ambient temperature, The resulting precipitation was filtered off and rapidly washed twice with ethanol (2×150 ml). The precipitate was then dried in vacuum over P$_2$O$_5$ to give the title compound (9.5 g), yield 90%.

1H NMR (D$_2$O). Two isomers in ratio 1:4. δ 0.90 (3H, t, minor form), 1.10 (3H, t, major form), 3.21 (3H, s, major form), 3.50 (3H, s, minor form), 3.50–3.70 (2H, m, minor form), 3.70–3.85 (2H, m, major form), 6.92–7.51 (8H, m, both forms).

EXAMPLE 5

1,2-Dihydro-4-hydroxy-5-chloro-1-methyl-2-oxo-quinoline-3-carboxylic acid ethyl ester Phosgene (51 g, 0.52 mol) dissolved in dioxane (150 ml) was added in portions to a mechanically stirred slurry of sodium bicarbonate (44 g, 0.52 mol) and 2-amino-6chlorobenzoic acid (30 g, 0.175 mol) in dioxane (300 ml). Violent reaction with gas evolution occurred and the reaction mixture was cooled to keep the temperature below 50° C. After 30 minutes the reaction mixture was kept at 50° C. for 1 hour. After cooling to 15° C. the resulting precipitate was collected, stirred with 50 ml of glacial acetic acid in 500 ml of water, collected again and dried to give the isatoic anhydride (30.3 g, 0.15 mol).

The anhydride was added slowly in portions to a mixture of sodium hydride (5.5 g, 0.18 mol) in 300 ml of N,N-dimethylformamide. After stirring at room temperature for 1 hour, methyl iodide (26 g, 0.18 mol) was added dropwise and stirring was continued for 2½ hours. The mixture was then added to 3 l of an ice/water slurry and the precipitate was collected and dried to yield the N-methylated isatoic anhydride (24.9 g, 0.118 mol).

The N-methylated anhydride was heated to 65° C. with sodium methoxide (6.3 g, 0.117 mol) in 130 ml of methanol for 1 hour. The solvents were evaporated. Water and dichloromethane were added and the organic layer was separated, dried and concentrated to yield an oily residue (22.7 g, 0.114 mol).

The residue above was dissolved in 300 ml of dichloromethane together with 4-aminopyridine (0.2 g) and triethylamine (7.1 ml). The solution was cooled and ethyl malonyl chloride (18.9 g, 0.125 mol) was slowly added. The mixture was stirred at room temperature for 4 hours and worked up to give a syrup. To this syrup was added 450 ml of ethanol and sodium methoxide (18.5 g, 0.342 mol) and the mixture was stirred for 3 hours. The solvents were evaporated and the residue was dissolved in 750 ml of water, washed with ethyl acetate and toluene and subsequently acidified with 5 M hydrochloric acid. The resulting precipitate was collected and dried to yield the title compound as a white powder (30 g, 0.106 mol) in a total yield of 60%.

1H NMR (CDCl$_3$) δ 1.46 (3H, t), 3.63 (3H, s), 4.49 (2H, q), 7.23 (1H, d), 7.27 (1H, d), 7.49 (1H, t), 15.0 (1H, s).

In essentially the same manner the following compounds are obtained from the corresponding starting materials:

1,2-dihydro-4-hydroxy-5-fluoro-1-methyl-2-oxo-quinoline-3-carboxylic acid ethyl ester, 1,2-dihydro-4-hydroxy-1,5-dimethyl-2-oxo-quinoline-3-carboxylic acid ethyl ester.

EXAMPLE 6

1,2-Dihydro-4-hydroxy-5-trifluoromethyl-1-methyl-2-oxo-quinoline-3-carboxylic acid ethyl 2-Fluoro-6-(trifluoromethyl)benzonitrile (10 g, 53 mmol) was warmed at 40° C. in anhydrous methylamine (200 ml) in an autoclave for 2 days. The excess methylamine was allowed to evaporate and the resulting grey solid was dissolved in dichloromethane (200 ml) together with 4-aminopyridine (0.1 g) and triethylamine (3.3 ml, 26 mmol). To this chilled solution was slowly added ethyl malonyl chloride (8.8 g, 60 mmol). The solution was stirred for 4 hours and then worked up to give a yellowish syrup. The syrup was dissolved in 100 ml of anhydrous ethanol and sodium methoxide (5.4 g, 0.1 mol) was added. After 1 hour, the solvent was removed and the residue worked up with dichloromethane and water. The quinoline derivative formed was carefully dried and then suspended in chilled anhlydrous tetrahydrofuran (250 ml). Sodium hydride (4 g, 0.125 mol) and then methyl iodide (10 ml, 0.15 mol) was slowly added. The mixture was heated under reflux for 6 hours, quenched with water and worked up with diethyl ether. The solvents were removed and the residue (17.3 g) was dissolved in a mixture of ethanol (50 ml) and conc. hydrochloric acid (10 ml). The solution was warmed at 45° C. during the night, cooled and the precipitate was collected to give 8 g of the title compound.

1H NMR (CDCl$_3$) δ 1.46 (3H, t), 3.68 (3H, s), 4.50 (2H, q), 7.58 (1H, m), 7.71 (2H, m), 15.0 (1H, s).

EXAMPLE 7

1,2-Dihydro-4-hydroxy-5-methoxy-1-methyl-2-oxo-quinoine-3-carboxylic acid ethyl ester To a solution of 2,6-difluorobenzonitrile (42 g, 0.3 mol) in 150 ml of anhydrous methanol was slowly added sodium methoxide (17.9 g, 0.33 mol) at 30° C. After being heated under reflux for 1 hour, aqueous 40% methylamine (133 ml, 1.2 mol) was added and the solution refluxed for 4 days. On cooling, a white solid precipitated which was collected by filtration. The solid, 2-methoxy-6-(methylamino) benzonitrile, was dissolved in an aqueous solution of ethylene glycol (500 ml) and potassium hydroxide (14 g). The solution was refluxed at 150° C. overnight, cooled to room temperature and the pH adjusted to 4 with conc. hydrochloric acid. The precipitate was collected by filtration, washed with water (50 ml) and dried under vacuum. The white solid, 5-methoxy-anthranilic acid (32 g, 0.18 mol), and sodium bicarbonate (38 g, 0.45 mol) were suspended in 1,4-dioxane (500 ml) and then phosgene (25 ml, 0.45 mol) was slowly added under cooling in an ice bath. The mixture was warmed at 40° C. for 1 hour, cooled to 15° C., water (150 ml) was added and the white solid collected by filtration. After being carefully dried, the solid (20.7 g, 0.1 mol) was added to a solution of sodium diethylmalonate (0.17 mol) in anhydrous N,N-dimethylformamide (250 ml) at room temperature. The solution was heated at 100° C. for 3 hours, cooled to room temperature, water (250 ml) was added and the pH adjusted to 4 with conc. hydrochloric acid. The precipitate was collected by filtration and dried under vacuum to give the title compound as pure white crystals, 22 g.

1H NMR (CDCl$_3$) δ 1.43 (t, 3H), 3.62(s, 3H), 3.96(s, 3H), 4.45(q, 2H), 6.70(d, 1H), 6.92(d, 1H), 7.55(t, 1H), 13.5(s, 1H).

EXAMPLE 8

1,2-dihydro 4-hydroxy-1-methyl-2-oxo-5,6-methylenedioxy-quinoline-3-carboxylic acid ethyl ester Di-tert-butyl dicarbonate (36 g, 0.17 mol) was added portionwise to a solution of 3,4-(methylenedioxy)-aniline (20.6 g, 0.15 mol) in anhydrous tetrahydrofuran (150 ml). The solution was reflux heated for 2 hours, then concentrated under vacuum to give a black solid residue. The residue was dissolved in anhydrous tetrahydrofuran (600 ml) and cooled to −40° C. A hexane solution of 1.3 M sec-butyllithium (265 ml, 0.35 mol) was added dropwise.

After stiring the solution for 0.5 hour at −40° C. dry ice (ca 40 g) pellets were added. The mixture was allowed to warm to 0° C. and water (ca 700 ml) was added. The aqueous solution was acidified with hydrochloric acid to pH 3 and extracted with ether. The extracts were dried and concentrated to give the N-tBoc protected 5,6-(methylenedioxy)anthranilic acid as a solid residue (45 g). This acid was added to an ice-cooled suspension of sodium hydride (80% in oil, 9.0 g, 0.30 mol) in N,N-dimethylformamide (200 ml). The mixture was stirred for 0.5 hour and methyl iodide (22 ml, 0.35 mol) was added. The mixture was stirred at room temperature overnight, was quenched with water (600 ml) and extracted three times with ether. The organic layer was washed with sat. brine, dried and concentrated under vacuum to give a darkbrown oil. The oil was dissolved in methanol (400 ml) and conc. hydrochloric acid (80 ml) was added. The solution was stirred overnight at room temperature, neutralised with 5 M sodium hydroxide and extracted three times with ether. The combined extracts were filtered through a column with SiO$_2$ and the eluate concentrated under vacuum to give the methylated anthranilic ester (20 g). The ester was dissolved in dichloromethane (400 ml) and cooled on an ice-bath. Ethyl malonyl chloride (21 g, 0.14 mol) was added and then, after 30 minutes, triethylamine (22 ml, 0.16 mol). After being stirred for 1 hour at room temperature the cloudy mixture was washed with 0.5 M hydrochloric acid and then bicarbonate. The organic phase was carefully dried and concentrated under vacuum. The residue was then dissolved in dry ethanol (200 ml) and sodium methoxide (17 g, 0.32 mol) was added. The mixture was stirred for 1 hour and water was added (300 ml). The solution was washed with ethyl acetate and then the aqueous solution was acidified with conc. hydrochloric acid. The precipitate was collected by filtration and dried under vacuum to give the title compound as grey crystals (17 g, overall yield 41%).

1H NMR (CDCl$_3$) δ 1.45 (3H, t), 3.58 (3H, s), 4.48 (2H, q), 6.17 (2H, s), 6.71 (1H, d), 7.14 (1H, d).

EXAMPLE 9

1,2-Dihydro-4-hydroxy-5-methoxy-1-methyl-2-oxo-quinoline-3-carboxylic acid

While cooling, 10 ml of conc. hydrochloric acid was added to 30 ml of acetic anhydride. To this solution, 1,2-dihydro-4-hydroxy-5-methoxy-1-methyl-2-oxo-quinoline-3-carboxylic acid ethyl ester (10.5 g, 38 mmol) was added and the mixture heated at 80° C. for 14 hours. The mixture was cooled to room temperature and the crystalline product was filtered off, washed with cold methanol and dried to give the title compound (7.2 g), yield 77%.

1H NMR ((CDCl$_3$) δ 3.73 (3H, s) 4.02 (3H, s), 6.82 (1H, d), 7.02 (1H, d), 7.62 (1H, t).

EXAMPLE 10

5-Ethyl isatoic anhydride

A mixture of chloral hydrate (59.3 g, 0.36 mol), water (700 ml), and sodium sulphate (85.8 g, 0.60 mol), was heated to 50° C. When 50° C. was reached, sequentially a mixture of 3-ethylaniline (40.8 g, 0.33 mol), water (700 ml) and conc. hydrochloric acid (33.6 ml) and a mixture of hydroxylamine hydrocloride (74.8 g, 1.04 mol) and water (330 ml) were added. The resulting mixture was heated to 80° C. during 30 minutes and kept for another 10 minutes at this temperature before the reaction mixture was cooled on an ice-bath. The resulting precipitate was filtered off, washed with water and dried in vacuum over P$_2$O$_5$ to give an isonitrosoacetanilide (36.6 g), yield 58%

The isonitrosoacetanilide (10.0 g, 0.05 mol), was added portionwise to a mixture of water (9 ml) and conc. sulphuric acid (60 ml) prewarmed to 50° C., maintaining the temperature between 50–55° C. When the addition was completed, the mixture was heated to 80° C. and kept at this temperature for 10 minutes. The reaction mixture was then cooled on an ice-bath and poured on 10–12 times the reaction volume of crushed ice. The mixture was then left standing for about one hour. The water suspension was extracted with dichloromethane which was dried and evaporated resulting in an mixture of the two analogues 4-ethyl and 6-ethyl isatins approximately 0.68:1 (7.6 g), yield 84%.

The mixture of the two isomers was dissolved in aqueous sodium hydroxide and the solution was filtered through celite and then acidified to pH 4. The 4-analogue was at this pH extracted into dichloromethane, which was dried and evaporated to give the pure 4-ethyl isatin (3.1 g), yield 34%.

4-Ethyl isatin (3.1 g, 0.018 mol) was added to a mixture of conc. sulphuric acid (45 l) in acetic acid (14 ml). The suspension was warmed to 30° C., hydrogen peroxide 35% (2.2 ml) was added and after the addition the temperature was raised to 65° C. After being heated for 3 hours, the mixture was cooled and the precipitate filtered off, washed with water and dried to give the title compound (1.7 g), yield 48%.

1H NMR (DMSO-$d_6$) δ 1.12 (3H, t), 3.02 (2H, q), 6.98 (1H, d), 7.05 (1H, d), 7.58 (1H, t), 11.6 (1H, broad).

Pharmacological methods

Acute experimental autoimmune encephalomyelitis (aEAE)

SJL/N female mice, 8 weeks of age, were used for the experiments. Mouse spinal cord homogenate (MSCH) was obtained from 8 to 12 weeks-old C57B1/6 female mice. The tissue was homogenised on ice and diluted in cold PBS. Incomplete Freund's containing 1 mg/ml *M. tuberculosis hominis* H37Ra was emulsified with an equal volume of MSCH to give a final concentration of 10 mg/ml of MSCH. The inoculum volume of 0.1 ml was injected intradermally at the base of the tail. Pertussis toxin was injected i.p. at day 0 and 3 after immunization. Treatment was given per os daily either at day 3 to 12 post-immunization or days 3 to 7 and 10 to 12. Control animals received saline. The animals, eight per dose group, were scored for clinical signs of paralytic disease on a scale from 0 to 5 in the following way; 0, normal; 1, limp tail; 2, hind limb paresis; 3 hind limb paralysis and limp foreleg; 4, bilateral hind and fore limb paralysis; 5, death. Clinical scores were monitored at day 7 and daily from day 9 until the end of the experiment at day 14. Treatment effect were calculated as percent inhibition of clinical scores compared to saline treated controls.

Collagen induced arthritis

DBA/1 male mice between 8 to 10 weeks of age were used for the experiments. On day 0 the mice were immunized intradermally at the base of the tail with bovine type II collagen (100 μg/mouse) in Freund's complete adjuvant. The treatment was given per os daily on days 3 to 7, 10 to 14, 17 to 21, 24 to 28 and 31 to 35. Fifteen days after immunization mice were inspected for signs of arthritis. The animals were inspected three times a week. Every second or tbird day individual paws of the arthritic animals were scored by a scale from 0–4 (0=no arthritis, 1=arthritis in one of the interphalangeal, metatarsophalangeal or intercarpal joints, 2=two arthritic joints, 3=three arthritic joints, 4=as in 3 but with more severe redness and swelling of the paw). The score for each paw was added to give a maximal attainable score of 16 for each mouse.

Ovalbumin-induced lung inflammation

C57B1/6 female mice between 10 to 14 weeks of age were used for the experiments, 10 mice/group. The mice were sensitized with ovalbumnin (OA) in aluminium hydroxide in a volume of 0.2 ml, inoculated ip. Treatment was given at day 0 to day 16. Control mice received saline. Fourteen days after the OA sensitization mice were exposed for 20 minutes to an aerosol of 1.5% w/v, of OA in saline produced by a nebulizer. Vehicle-challenged control mice were exposed to saline. Seventy-two hours after OA/vehicle challenge, mice were anaesthetised and bronchoalveolar lavage was performed by instilling 0.5 ml ice-cold phosphate buffered saline (PBS) into the lungs twice. Total cell counts were determined and differential counts were made based on identification of eosinophils, monocytes/alveolar macrophages, lymphocytes and neutrophils. Eosinophil infiltration into the lung tissue was evaluated by histochemical methods on frozen lung sections using diaminobenzidine tetrahydrochloride (DAB).

Teratogenic effects in the rat

The compounds were administered subcutaneously to female rats during day 8 to 14 of pregnancy. The rats were caesarean sectioned and necropsied on day 20 after fertlisation. The foetuses were examined for external and internal abnormalities.

Beagle Pain Syndrome (BPS)

The compounds were administrated intravenously to beagle dogs. The dosage was given for five consecutive days. The dogs were evaluated for clinical and laboratory signs of the pain syndrome, e.g., fever, increased erythrocyte sedimentation rate (ESR), alkaline phosphate (AP), induction of acute phase proteins and vasculitis.

Preferred compounds are N-ethyl-N-phenyl-1,2dihydro-4-hydroxy-5-chloro-1-metbyl-2-oxo-quinoline-3-carboxamide, N-ethyl-N-phenyl-1,2-dihydro-4-hydroxy-5-methoxy-1-methyl-2-oxo-quinoline-3-carboxamide, N-ethyl-N-phenyl-1,2-dihydro-4-hydroxy-5-bromo-1-methyl-2-oxo-quinoline-3-carboxamide and N-ethyl-N-phenyl-1,2-dihydro-4-hydroxy-5,6-methylenedioxy-1-methyl-2-oxo-quinoline-3-carboxamide hereinafter called Compound B, C, D and E, respectively. Roquinimex and N-ethyl-N-phenyl-1,2-dihydro-4-hydroxy-1-methyl-2-oxo-quinoline-3-carboxamide and N-methyl-N-phenyl-1,2-dihydro-4-hydroxy-5-chloro-1-methyl-2-oxo-quinoline-3-carboxamide hereinafter called Compound F and G, respectively, are included as reference compounds:

aEAE inhibition

| Dose, mg/kg p.o. | % aEAE Inhibition | | | |
|---|---|---|---|---|
| | Compound B (invention) | Compound C (invention) | Compound F | Roquinimex |
| 0.04 | 60 | 48 | not tested | not tested |
| 0.2 | 74 | 71 | not tested | 35 |
| 1 | 98 | 73 | not tested | 40 |
| 5 | 96 | 90 | 63 | 69 |

Arthritic score, type II collagen induced arthritis

| Compound (dose 5 mg/kg p.o.) | Incidence (%) day 35 | Mean score day 35 |
|---|---|---|
| D (invention) | 30 | 0.4 |
| E (invention) | 10 | 0.1 |
| Roquinimex | 50 | 1.7 |

Embryotoxicity - external malformations

| Dose, mg/kg (route) | % malformed foetuses | | |
|---|---|---|---|
| | Compound B (invention) | Compound G | Roquinimex |
| 6 | 0[a] | 37[a] | |
| 10 | | | 9[b] |
| 30 | 1[a] | Not tested | 30[b] |

[a] route s.c.
[b] route p.o.

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, sterile solutions for parental administration, suppositories for rectal administration or suitable topical formulations. Conventional procedures for the selection and preparation of suitable pharmaceutical formulations are described, for example, in "Pharmaeuticals—The Science of Dosage Form Design", M. B. Aulton, Churchill Livingstone, 1988.

A suitable daily dose for use in the treatment of MS is contemplated to vary between 0.0005 mg/kg to about 10 mg/kg body weight, in particular between 0.005 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

References

1. Talal, N.: Autoimmune diseases. In: Roitt, I. M. and Delves, P. J. (eds.) Encyclopedia of Immunology, pp. 195–198. Academic Press, 1992.

2. Prineas, J. W.: The neuropathology of multiple sclerosis. In: Koetsier, J. C. (ed) Handbook of Clinical Neurology, pp. 213–257. Elsevier Science Publ., Amsterdam, 1985.

3. Tarkowski, A., Gunnarsson, K., Nilsson. L. -Å., Lindholm, L. and Stålhandske, T. Successful treatment of autoimmunity in MRL/1 mice with LS2616, a new immunomodulator. Arthritis Rheum. 29(11): 1405–1409, 1986.

4. Larsson, E. -L., Joki, A. -L. and Stålhandske, T, Mechanism of action of the new immunomodulator LS2616 on T-cell responses. Int J Immunopharmacol 9(4): 425–31, 1987.

5. Wanders, A., Larsson, E., Gerdin, B. and Tufveson G. Abolition of the effect of cyclosporine on rat cardiac allograft rejection by the new immunomodulator LS-2616 (Linomide). Transplantation 47(2): 216–217, 1989.

6. Kalland, T. Regulation of natural killer progenitors: studies with a novel immunomodulator with distinct effects at the precursor level. J Immunol 144(11): 4472–4476, 1990.

7. Gonzalo, J. A., González-García, A., Kalland, T., Hedlund, G., Martinez, C. and Kroemer, G. Linomide, a novel immunomodulator that prevents death in four models of septic shock. Eur J Immunol 23: 2372–2374, 1993.

8. Karussis, D. M., Lehmann, D., Slavin, S. et al. Treatment of chronic-relapsing experimental autoimmune encephalomyelitis with the syntethic immunomodulator Linomide (quuioline-3carboxamide). Proc Natl Acad Sci USA 90: 6400–6404, 1993.

9. Gonzalo, J. A., González-Garcia, A., Kalland, T. et al. Linomide inhibits programmed cell death of peripheral T cells in vivo. Eur J Immunol. 24: 48–52, 1994.

10. Gross, D. J., Sidi, H., Weiss, L., Kalland, T., Rosenmann, E. and Slavin, S. Prevention of diabetes mellitus in non-obese diabetic mice by Linomide, a novel immunomodulating drug. Diabetologia 37: 1195–1201, 1994.

11. Karussis, D. M., Lehmannn, D., Brenner, T. et al. Immunomodulation of experimental autoimmune myasthenia gravis with Linomide. J Neuroimmunol 55(2): 187–193, 1994.

12. Bai, X. F., Shi, F. D., Zhu, J., Xiao, B. G., Hedlund, G. and Link, H. Linomide-induced suppression of experimental autoimmune neuritis is associated with down-regulated macrophage functions. J Neuroimmunol 76:177–184 1997.

13. Karussis, D. M. Meiner, Z., Lehmann, D. et al. Treatment of secondary progressive multiple sclerosis with the immunomodulator Linomide. Neurology 47: 341–346, 1996.

14. Andersen, O., Lycke, J., Tollesson, P. O. et al. Linomide reduces the rate of active lesions in relapsing-remitting multiple sclerosis. Neurology 47: 895–900, 1996.

15. Kelly, D. F., Grimsell C. S. G. and Kenyon, C. J. Polyarteritis in the dog: A case report. Vet Record 92: 363–366, 1973.

16. Harcourt, R. A. Polyarterites in a colony of beagles. Vet Record 102: 519–522, 1978.

We claim:

1. A compound of formula (I)

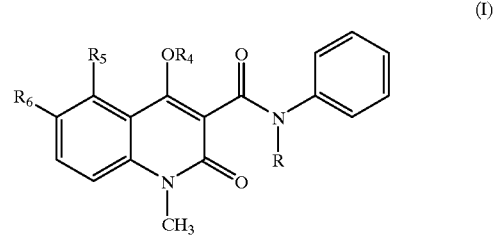

wherein
R is ethyl, n-propyl, iso-propyl, n-butyl, iso-butyl, sec-butyl or allyl;
$R_4$ is hydrogen or a pharmaceutically acceptable organic or inorganic cation;
$R_5$ is methyl, ethyl, n-propyl, iso-propyl, methoxy, ethoxy, chloro, bromo, $CF_3$, or $OCH_xF_y$; wherein
x=0–2
y=1–3 with the proviso that
x+y=3;
$R_6$ is hydrogen; or
$R_5$ and $R_6$ taken together are methylenedioxy; or any tautomer thereof.

2. The compound according to claim 1 wherein the pharmaceutically acceptable inorganic cations are derived from sodium, potassium and calcium, and the organic cations are derived from monoethanolamine, diethanolamine, dimethylaminoethanol, and morpholine.

3. The compound according to claim 1 wherein $R_5$ is methyl, ethyl, methoxy, chloro, or bromo.

4. The compound according to claim 3 wherein R is ethyl or n-propyl.

5. The compound according to claim 4 wherein $R_4$ is selected from hydrogen and sodium.

6. The compound according to claim 1, N-ethyl-N-phenyl-1,2-dihydro-4-hydroxy-5-methyl-1-methyl-2-oxo-quinoline-3-carboxamide.

7. The compound according to claim 1, N-ethyl-N-phenyl-1,2-dihydro-4-hydroxy-5-ethyl-1-methyl-2-oxo-quinoline-3-carboxamide.

8. The compound according to claim 1, N-ethyl-N-phenyl-1,2-dihydro-4-hydroxy-5-methoxy-1-methyl-2-oxo-quinoline-3-carboxamide.

9. The compound according to claim 1, N-ethyl-N-phenyl-1,2-dihydro-4-hydroxy-5-chloro-1-methyl-2-oxo-quinoline-3-carboxamide or its sodium salt.

10. The compound according to claim 1, N-ethyl-N-phenyl-1,2-dihydro-4-hydroxy-5-bromo-1-methyl-2-oxo-quinoline-3-carboxamide.

11. The compound according to claim 1, N-ethyl-N-phenyl-1,2-dihydro-4-hydroxy-5,6-methylenedioxy-1-methyl-2-oxo-quinoline-3-carboxamide.

12. A pharmaceutical composition comprising as active ingredient a compound having the formula (I) according to claim 1 together with a pharmaceutically acceptable carrier.

13. The pharmaceutical composition according to claim 12 in a dosage form sufficient to provide a daily dose of said compound of 0.0005 mg/kg to about 10 mg/kg body weight.

14. A process for manufacturing of a compound of formula (I) by (A) reacting an ester derivative of the quinolne carboxylic acid of formula (II),

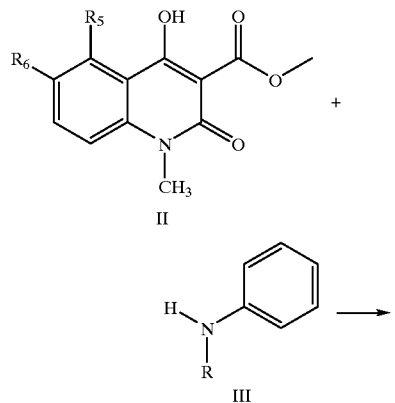

with an aniline of formula (III) in a solvent; or (B) reacting an isatoic anhydride of formula (IV), with an N-alkyl-N-phenylcarbamoyl acetic acid alkyl ester of formula (V),

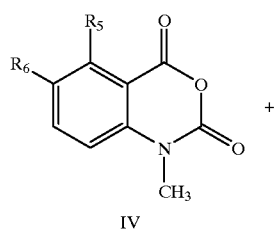

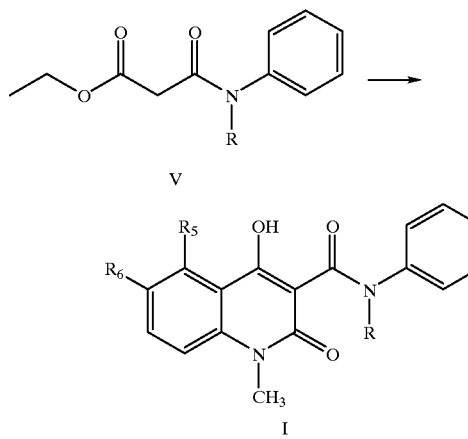

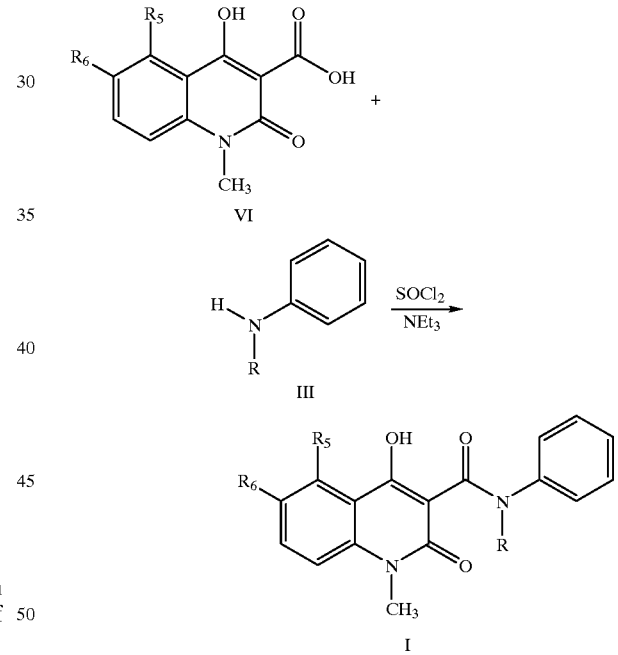

using a strong base, in a solvent; or (C) reacting a quinoline caxboxylic acid of formula (VI) with an aniline of formula (III), using a coupling reagent, in the presence of triethylamine and a solvent.

15. A method of treating a mammal suffering from a disease resulting from autoimmunity or pathological inflammation comprising administering to said mammal an effective amount of a compound having the formula (I)

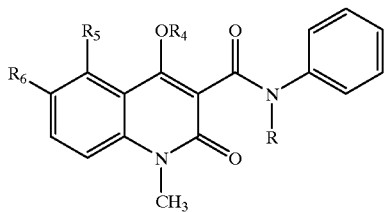

(I)

wherein

R is ethyl, n-propyl, iso-propyl, n-butyl, iso-butyl, sec-butyl or allyl;

$R_4$ is hydrogen or a pharmaceutically acceptable inorganic or organic cation;

$R_5$ is methyl, ethyl, n-propyl, iso-propyl, methoxy, ethoxy, chloro, bromo, $CF_3$, or $OCH_xF_y$; wherein
x=0–2,
y=1–3 with the proviso that
x+y=3;

$R_6$ is hydrogen; or $R_5$ and $R_6$ taken together are methylenedioxy; or any tautomer thereof.

16. A method according to claim 15 wherein the pharmaceutically acceptable inorganic cations are derived from sodium, potassium and calcium, and the organic cations are derived from monoethanolamine, diethanolamine, dimethylaminoethanol, and morpholine.

17. The method according to claim 15 wherein $R_5$ is methyl, ethyl, methoxy, chloro or bromo.

18. The method according to claim 16 wherein R is ethyl or n-propyl.

19. The method according to claim 17 wherein R4 is hydrogen or sodium.

20. The method according to claim 15 wherein the compound as administered is N-ethyl-N-phenyl-1,2-dihydro-4-hydroxy-5-chloro-1-methyl-2-oxo-quinoline-3-carboxamide or its sodium salt.

21. The method according to claim 15 of treating a mammal suffering from multiple sclerosis (MS).

22. The method according to claim 15 of treating a mammal suffering from insulin-dependent diabetes mellitus (IDDM).

23. The method according to claim 15 of treating a mammal suffering from systemic lupus erythematosus (SLE).

24. The method according to claim 15 of treating a mammal suffering from rheumatoid arthritis (RA).

25. The method according to claim 15 of treating a mammal suffering from inflammatory bowel disease (IBD).

26. The method according to claim 15 of treating a mammal suffering from psoriasis.

27. The method according to claim 15 of treating a mammal suffering from inflammatory respiratory disorder.

28. The method according to claim 15 of treating a mammal suffering from atherosclerosis.

29. The method according to claim 17 of treating a mammal suffering from stroke.

30. The method according to claim 17 of treating a mammal suffering from Alzheimer's disease.

31. The compound according to claim 2, wherein $R_5$ is methyl, ethyl, methoxy, chloro or bromo.

32. The compound according to claim 2 wherein R is ethyl or n-propyl.

33. The compound according to claim 2 wherein $R_4$ is hydrogen or sodium.

34. The composition of claim 12, wherein said dosage form is sufficient to provide a daily dose of 0.005 to 1 mg/kg of body weight.

35. The method according to claim 27 wherein said disorder is asthma.

36. The method according to claim 16 of treating a mammal suffering from multiple sclerosis, insulin-dependent diabetes mellitus, systemic lupus erythematosus, rheumatoid arthritis and inflammatory bowel disease, psoriasis, inflammatory respiratory disorder, atherosclerosis, stroke or Alzheimer's disease.

37. The method according to claim 17 of treating a mammal suffering from multiple sclerosis, insulin-dependent diabetes mellitus, systemic lupus erythematosus, rheumatoid arthritis and inflammatory bowel disease, psoriasis, inflammatory respiratory disorder, atherosclerosis, stroke or Alzheimer's disease.

38. The method according to claim 18 of treating a mammal suffering from multiple sclerosis, insulin-dependent diabetes mellitus, systemic lupus erythematosus rheumatoid arthritis and inflammatory bowel disease, psoriasis, inflammatory respiratory disorder, atherosclerosis, stroke or Alzheimer's disease.

39. The method according to claim 21 of treating a mammal suffering from multiple sclerosis, insulin-dependent diabetes mellitus, systemic lupus erythematosus, rheumatoid arthritis and inflammatory bowel disease, psoriasis, inflammatory respiratory disorder, atherosclerosis, stroke or Alzheimer's disease.

40. A process according to claim 14 wherein in reaction (A) said ester derivative of formula II is the methyl or ethyl ester, and the solvent is toluene, xylene;

in reaction (B) said acidic acid alkyl ester of formula V is the methyl or ethyl ester, the strong base is sodium hydride and said solvent is N,N-dimethyl acetamide; or in reaction (C) said coupling reagent is a carbodiimide or thionyl chloride, and said solvent is dichloromethane.

* * * * *

UNITED STATES PATENT AND TRADEMARK OFFICE
CERTIFICATE OF CORRECTION

PATENT NO.   : 6,077,851
DATED        : June 20, 2000
INVENTOR(S)  : Björk et al.

It is certified that error appears in the above-identified patent and that said Letters Patent is hereby corrected as shown below:

Column 2,
Line 15, delete "4hydroxy" and insert therefor -- 4-hydroxy --;

Column 9,
Line 61, delete "6chloro" and insert therefor -- -6-chloro --;

Column 10,
Line 42, after "ethyl" insert -- ester --;

Column 13,
Line 44, delete "tbird" and insert therefor -- third --;

Column 14,
Line 15, delete "1,2dihydro" and insert therefor -- 1,2-dihydro --;
Line 16, delete "1-metbyl" and insert therefor -- 1-methyl --.

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,077,851 | Page 1 of 1 |
| APPLICATION NO. | : 09/296519 | |
| DATED | : June 20, 2000 | |
| INVENTOR(S) | : Björk et al. | |

It is certified that error appears in the above-identified patent and that said Letters Patent is hereby corrected as shown below:

Column 20, line 39 claim 38, should read --The method according to claim 19 of treating a--.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,077,851 | Page 1 of 1 |
| APPLICATION NO. | : 09/296519 | |
| DATED | : June 20, 2000 | |
| INVENTOR(S) | : Björk et al. | |

It is certified that error appears in the above-identified patent and that said Letters Patent is hereby corrected as shown below:

Column 20, line 39 claim 39, should read --The method according to claim 19 of treating a--.

This certificate supersedes the Certificate of Correction issued September 15, 2009.

Signed and Sealed this

Twenty-third Day of February, 2010

David J. Kappos
*Director of the United States Patent and Trademark Office*